(12) United States Patent
Nokita (10) Patent No.: US 6,795,528 B2
(45) Date of Patent: Sep. 21, 2004

(54) RADIOGRAPHIC APPARATUS, RADIOGRAPHIC METHOD, AND COMPUTER-READABLE STORAGE MEDIUM

(75) Inventor: Makoto Nokita, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/035,154

(22) Filed: Jan. 4, 2002

(65) Prior Publication Data

US 2002/0101960 A1 Aug. 1, 2002

(30) Foreign Application Priority Data

Jan. 12, 2001 (JP) ......................................... 2001-005563

(51) Int. Cl.$^7$ .............................................. G21K 1/00
(52) U.S. Cl. ...................................................... 378/155
(58) Field of Search ............................ 378/95, 96, 98.7, 378/108, 154, 155

(56) References Cited

U.S. PATENT DOCUMENTS

| | | | | |
|---|---|---|---|---|
| 3,916,192 A | * | 10/1975 | Schmitmann et al. | 378/98 |
| 4,160,906 A | * | 7/1979 | Daniels et al. | 378/97 |
| 4,403,337 A | * | 9/1983 | Kleinman | 378/95 |
| 4,731,806 A | * | 3/1988 | Takahata | 378/155 |
| 4,797,905 A | * | 1/1989 | Ochmann et al. | 378/108 |
| 4,803,716 A | * | 2/1989 | Ammann et al. | 378/155 |
| 5,218,625 A | * | 6/1993 | Heidsieck | 378/97 |
| 5,305,369 A | * | 4/1994 | Johnson et al. | 378/155 |
| 5,379,333 A | * | 1/1995 | Toth | 378/16 |
| 5,379,335 A | * | 1/1995 | Griesmer et al. | 378/155 |
| 5,559,851 A | * | 9/1996 | Schmitt | 378/155 |
| 5,666,395 A | * | 9/1997 | Tsukamoto et al. | 378/98.4 |
| 5,737,386 A | * | 4/1998 | Strawder | 378/95 |
| 6,088,427 A | * | 7/2000 | Pagano | 378/155 |
| 6,157,700 A | * | 12/2000 | Sako | 378/98.12 |
| 6,167,115 A | * | 12/2000 | Inoue | 378/155 |
| 6,178,228 B1 | * | 1/2001 | Schol | 378/162 |
| 6,181,773 B1 | * | 1/2001 | Lee et al. | 378/155 |
| 6,244,507 B1 | * | 6/2001 | Garland et al. | 235/383 |
| 6,259,767 B1 | * | 7/2001 | Neumann et al. | 378/151 |
| 6,480,574 B2 | * | 11/2002 | Goto | 378/154 |
| 2002/0001366 A1 | * | 1/2002 | Tamura et al. | 378/155 |

* cited by examiner

Primary Examiner—David V. Bruce
Assistant Examiner—Allen C. Ho
(74) Attorney, Agent, or Firm—Fitzpatrick, Cella, Harper & Scinto (57) ABSTRACT

A radiographic apparatus is disclosed which controls a movement of a reciprocatingly moving grid so that the grid is not or less likely returned in the middle of exposure of an object to X rays. The probability that the object is still exposed to the X rays when the grid is moved in the vicinity of a turning point is thus substantially lowered. Therefore the probability that a resulting radiograph has no or less moire pattern due to the grid is substantially heightened.

5 Claims, 9 Drawing Sheets

RADIOGRAPHIC APPARATUS, RADIOGRAPHIC METHOD, AND COMPUTER-READABLE STORAGE MEDIUM

BACKGROUND OF THE INVENTION

1. Field of the Invention

The present invention relates to a radiographic apparatus, a radiographic method, and a computer-readable recording medium, which can use a scattered radiation removal grid for removing radiation scattered by and within an object when the object is radiographed.

2. Description of the Related Art

Radiographing such as X-ray imaging has been used in diagnosis in medical practice, and examination and test of industrial products, for example. In X-ray imaging, an object is exposed to X rays, and X rays transmitted through the object are used to photosensitize a film or a screen. An X-ray image is thus obtained. The X rays transmitted through the object contain X rays linearly transmitted through the object and X rays that have been scattered within the object and then transmitted therethrough (hereinafter referred to as "scattered X rays"). In X ray imaging, the scattered X rays degrade the contrast of an X ray image, thereby substantially affecting the quality of the X-ray image.

A scattered X ray removal grid (hereinafter simply referred to as a "grid") is arranged parallel to the plane of imaging to efficiently remove the scattered X rays thereby improving the contrast of the X-ray image. The grid is formed of lead foils that are arranged so as to focus toward a focal point of an X-ray source, or lead foils that are arranged perpendicular to the imaging plane. The grid facilitates the transmission of X rays that have entered after being linearly transmitted through the object from the focal point of the X-ray source while blocking the X rays that are incident at a slant angle after being scattered within the object.

In the conventional X-ray imaging using a film/screen system with the grid, the frequency of stripe-like lead foils of grid (i.e., the reciprocal number of the pitch of the lead foils, also referred to as a "grid frequency" or a "grid density") is typically set higher than a frequency component of an ordinary X-ray image (on the assumption that no grid is employed) so that a striped pattern, occurring due to the grid in the X-ray image, is inconspicuous. By moving the grid in parallel to the imaging plane, the contrast of the striped pattern occurring due to the grid is reduced to make the striped pattern less visible or invisible in the X-ray image.

Digital radiographic apparatuses have been used. The digital radiographic apparatus obtains X-ray image data by converting the X rays transmitted through the object into visible light rays proportional to the intensity of the X rays through a fluorescent material (scintillator), converting the visible light rays into electrical signals through a photoelectric conversion element comprising a plurality of pixels, and (analog-to-digital) converting the electrical signals by an AD converter. Digital radiographic apparatuses of a sort begin to be used which obtain X-ray image data by sensing the distribution of electric charges proportional to the intensity of X rays that result from directly absorbing (through photoelectric conversion) X rays transmitted through an object, converting the charges into electrical signals, and (analog-to-digital) converting the electrical signals through an AD converter.

The above-mentioned digital radiographic apparatuses present an X-ray absorption ratio higher than that of the conventional film/screen system, and is free from a mottle structure that degrades granularity of an image in the conventional film/screen system. An X-ray image obtained from the above-mentioned digital radiographic apparatus is a digital image. Therefore the X-ray image is not necessarily output with a predetermined tone scale characteristics the same as that used in a film/screen system. Observing an X-ray image on a monitor, a user may freely change the tone scale characteristics. The user is also free to perform image processing such as frequency analysis, frequency enhancement or suppression processing or the like on the resulting X-ray image, thereby improving image quality.

The digital radiographic apparatus using the above-mentioned scattered X ray removal grid suffers from a moire pattern (a striped pattern, here) which does not exist in the X-ray image in the conventional film/screen system. The moire pattern is generated on the basis of a difference between the pixel pitch of a sensor for sensing the X ray as an electrical signal and the pitch of the lead foils forming the grid (the reciprocal number of the grid density). Let Ny represent the Nyquist frequency of the sensor and Gy represent the grid frequency (the grid density), and the frequency of the moire pattern is expressed as 2 Ny−Gy.

For example, when the Nyquist frequency Ny is 2.5 lp/mm (the pixel pitch of the sensor is 200 μm) and the grid frequency Gy is 4.0 lp/mm (40 lines/cm), the frequency of the moire pattern is 1.0 lp/mm. Since this frequency component is the one appearing in the typical X-ray images, the moire pattern is distinctly visible, thereby substantially degrading the quality of the resulting X-ray images. Here, lp/mm stands for line pairs per mm. The resolving power of the radiographic apparatus is sometimes measured using a chart having lead lines. The resolving power is defined by referring to how many pairs of the presence and absence of the lead line are recognized per unit length.

With the advance of technology, the digital radiographic apparatus provides an X-ray absorption ratio and resolving power higher than those of the conventional film/screen radiographic apparatus using the film/screen system. Viewing the screen of a monitor, the user is free to change the tone scale of the X-ray image. Therefore the component of the moire pattern having some contrast, as opposed in the conventional X-ray imaging, becomes a problem. Accordingly, a movement method of the grid different from that in the conventional film/screen system and a radiographing method accounting for the movement method are needed to make the moire pattern removed or inconspicuous.

SUMMARY OF THE INVENTION

Accordingly, it is an object of the present invention to provide a radiographic apparatus, a radiographic method, and a computer-readable storage medium for acquiring a radiograph, wherein the probability that a moire pattern is not generated or, is inconspicuous in the radiograph is heightened.

In one aspect of the present invention, a radiographic apparatus for obtaining a radiograph of an object includes a grid movement controller for controlling a movement of a grid which can move reciprocatingly, an input unit for inputting a method parameter relating to a radiographic method, and an imaging controller for setting a movement parameter relating to the movement of the grid to be used by said grid movement controller based on the method parameter input by the input circuit.

In another aspect of the present invention, a radiographic method for obtaining a radiograph of an object, includes the steps of controlling a movement of a grid which can move reciprocatingly, inputting a method parameter relating to a radiographic method, and setting a movement parameter relating to the movement of the grid to be used in said grid movement controlling step based on the method parameter input in said inputting step.

Further objects, features, and advantages of the present invention will be apparent from the following description of the preferred embodiments with reference to the attached drawings.

DESCRIPTION OF THE PREFERRED EMBODIMENTS

One embodiment of the present invention is now discussed, referring to the drawings.

Figure 1:
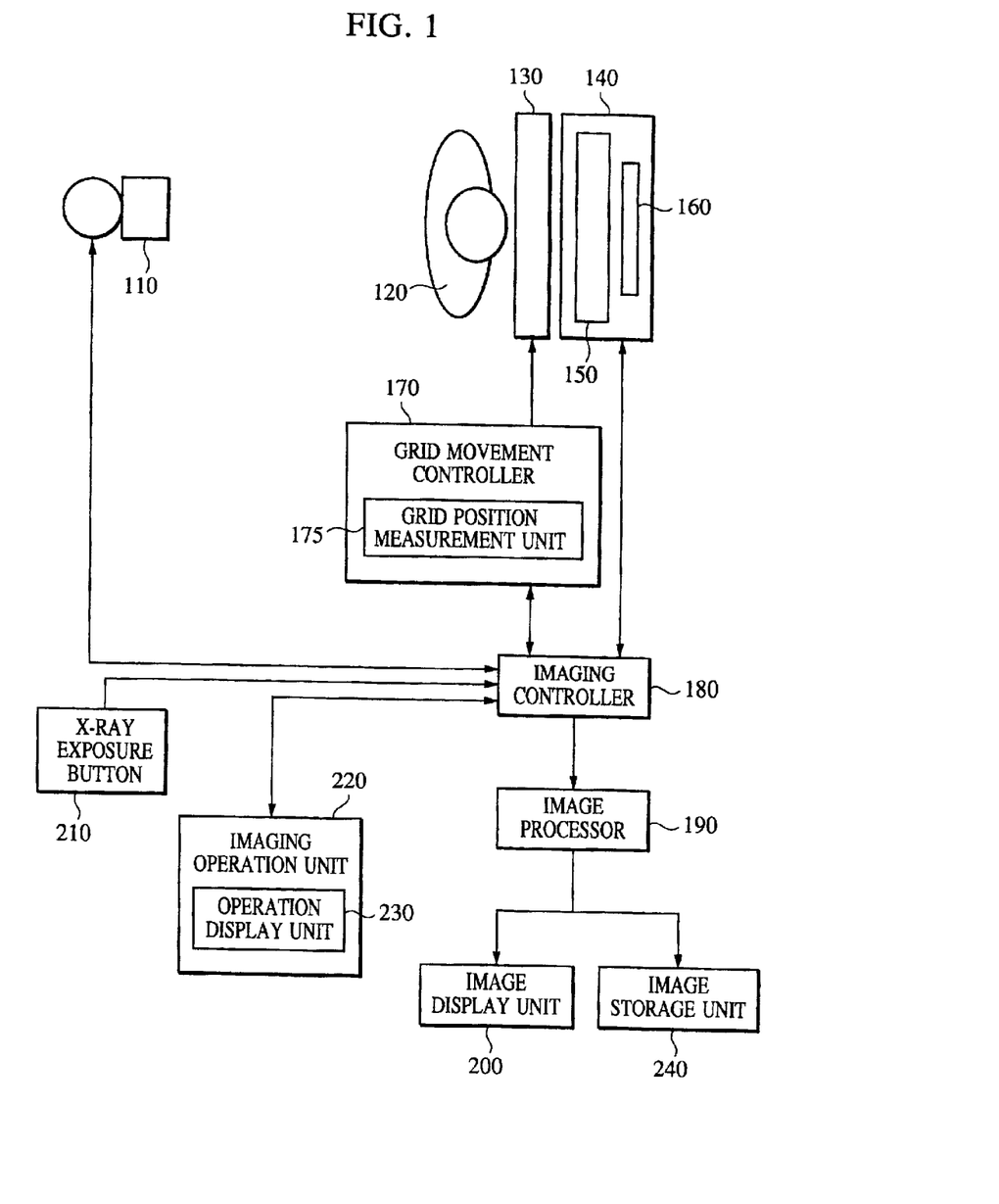
FIG. 1 is a block diagram showing an X-ray digital radiographic apparatus in accordance with one embodiment of the present invention.

FIG. 1 is a block diagram showing a digital radiographic apparatus in accordance with one embodiment of the present invention.

Referring to FIG. 1, an X-ray emitter 110, i.e., an X-ray source, emits and directs X rays to an object 120 during X-ray imaging. A grid 130 removes scattered X rays that have been generated within the object 120 which scatters X-ray emitted from the X-ray emitter 110.

A sensor 140 senses the X rays transmitted through the object 120 to obtain an X-ray image (a radiograph) of the object 120, and includes an X-ray image acquisition unit 150 and an X-ray timing acquisition unit 160. The X-ray image acquisition unit 150 detects the X rays transmitted through the object 120, converts the X rays into an electrical signal in accordance with the intensity of the X rays, and further converts the electrical signal from analog to digital to obtain an X-ray image. The X-ray timing acquisition unit 160 detects the X rays emitted from the X-ray emitter 110 and transmitted through the object 120 on a time division basis.

A grid movement controller 170 includes a grid position measurement unit 175. In response to the results of a measurement by the grid position measurement unit 175 and a command from an imaging controller 180, the grid movement controller 170 controls the movement of the grid 130 while assuring alignment with the timing of the X-ray imaging. The grid position measurement unit 175 under the control of the grid movement controller 170 measures the position of the grid 130.

The imaging controller 180 controls X-ray imaging by commanding that the grid 130 should be moved and by driving the sensor 140. An image processor 190 processes an X-ray image acquired by the X-ray image acquisition unit 150 so that a user may easily recognize the image. An image display unit 200 displays the X-ray image processed by the image processor 190. An image storage unit 240 stores the X-ray image processed by the image processor 190.

Pressing an X-ray exposure button 210 starts the X-ray imaging. An imaging operation unit 220, including an operation display unit 230, receives various parameters which the user inputs to control the X-ray imaging. The operation display unit 230 with the display or the touch screen thereof displays imaging operation items input via the imaging operation unit 220.

When the user presses the X-ray exposure button 210, the above-described digital radiographic apparatus directs the X rays to the object 120 from the X-ray emitter 110 in response to a command of the imaging controller 180. The X rays, emitted from the X-ray emitter 110 and transmitted through the object 120, enter the sensor 140 through the moving grid 130.

The X rays incident on the sensor 140 are detected by the X-ray image acquisition unit 150 in the sensor 140 in the form of an electrical signal. The X-ray image acquisition unit 150 also converts the electrical signal into a digital signal. The X-ray image in the digital form is then fed to the image processor 190 through the imaging controller 180.

The image processor 190 improves image quality by subjecting the X-ray image to a predetermined image processing, thereby displaying the X-ray image on the image display unit 200 or storing the X-ray image in the image storage unit 240 or both.

During X-ray imaging, the imaging controller 180 controls the grid movement controller 170 and the sensor 140 on the basis of the timing at which the X-ray emitter 110 expose the object 120 to the X rays. In this way, the timing of the irradiation of the X rays from the X-ray emitter 110 matches the timing of the movement of the grid 130 and the driving of the sensor 140.

Discussed in greater detail below is the timing of the imaging controller 180 for controlling the driving of the grid movement controller 170 and the sensor 140, and the grid movement controller 170 for controlling the movement of the grid 130.

The grid movement controller 170 for controlling the movement of the grid 130 is discussed below.

Figure 2:
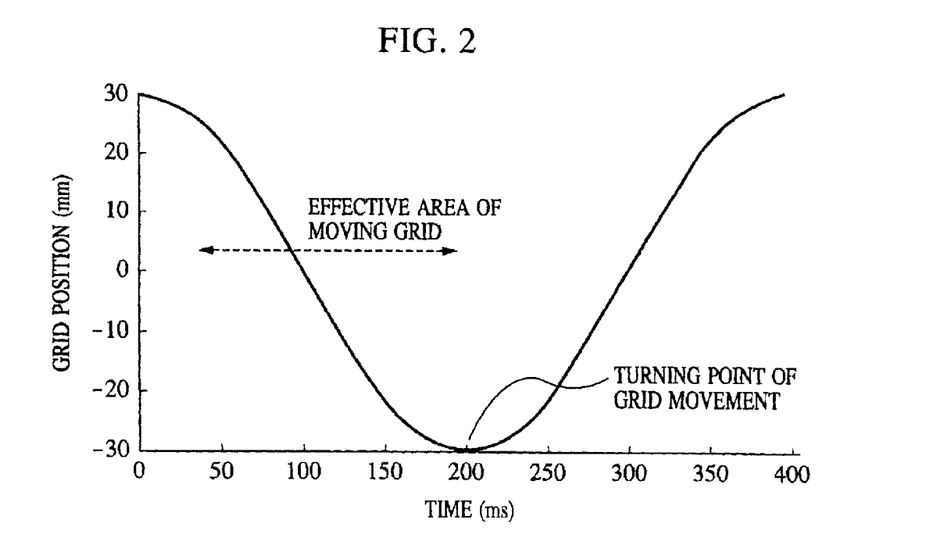
FIG. 2 is a graph plotting the interrelationship between an elapsed time from the beginning of movement of a grid and a position of the grid.
Figure 4:
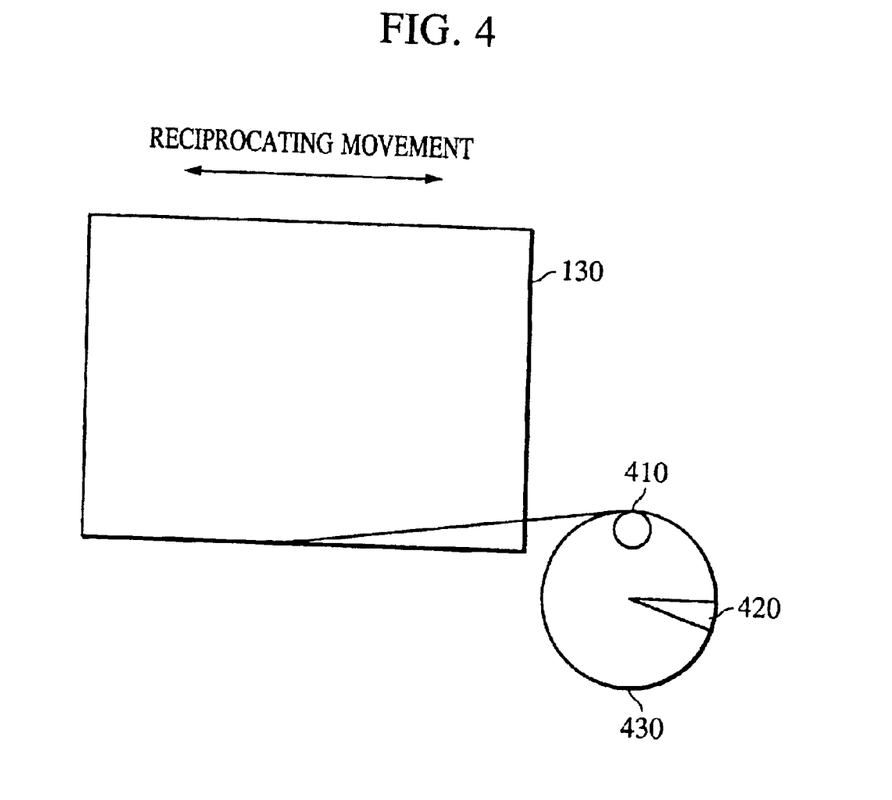
FIG. 4 illustrates the construction of a grid position measurement unit.

Referring to FIG. 4, the grid movement controller 170 moves the grid 130 using a link mechanism that converts a rotary motion of a pulse motor (shown in FIG. 4) into a linearly reciprocating motion (shown in FIG. 2).

FIG. 2 is a graph plotting the interrelationship between an elapsed time from the beginning of movement of the grid 130 and the position of the grid 130 relative to the sensor 140. The abscissa represents the elapsed time from the beginning of the movement, while the ordinate represents the position of the grid 130 relative to the sensor 140.

Figure 3:
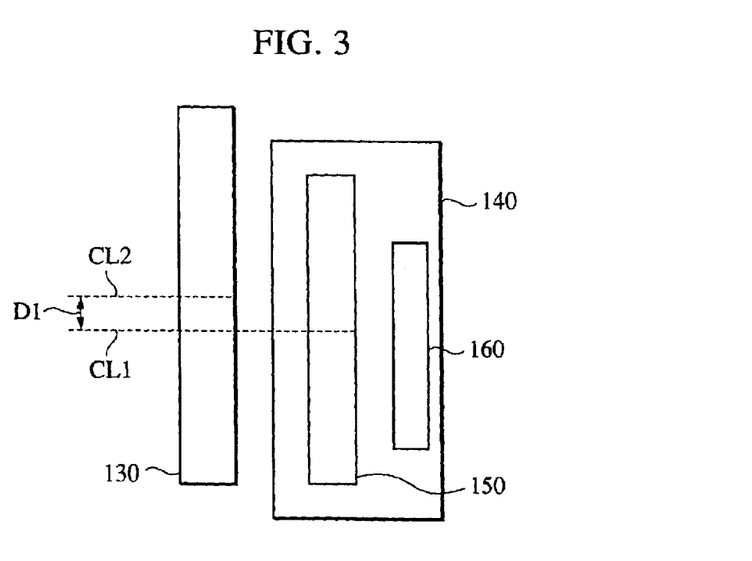
FIG. 3 illustrates the interrelationship between the grid and a sensor.

FIG. 3 illustrates the position of the grid 130 of FIG. 2 with respect to the sensor 140, viewed from above the grid 130 and the sensor 140. Referring to FIG. 3, blocks identical to those described with reference to FIG. 1 are designated with the same reference numerals, and the discussion thereof is omitted.

Referring to FIG. 3, CL1 designates the center line of the X-ray image acquisition unit 150 in the sensor 140, and CL2 designates the center line of the grid 130. D1 is the distance between the center line CL1 and the center line CL2. The position of the grid 130 with respect to the sensor 140 is regarded as having a positive value when the center line CL2 of the grid 130 is located to the right of the center line CL1 of the X-ray image acquisition unit 150 (i.e., with the center line CL2 below the center line CL1 in FIG. 3) if the X-ray image acquisition unit 150 is viewed from the unshown X-ray emitter 110. The position of the grid 130 with respect to the sensor 140 is regarded as having a negative value when the center line CL2 of the grid 130 is located to the left of the center line CL1 of the X-ray image acquisition unit 150 (i.e., with the center line CL2 above the center line CL1 in FIG. 3). The position of the grid 130 with respective to the sensor 140 shown in FIG. 3 has a negative value (of −30 mm).

In the interrelationship between the elapsed time from the beginning of the movement of the grid 130 and the position of the grid 130 with respect to the sensor 140 as shown in FIG. 2, the grid 130 starts moving from a point 30 mm right of the center of the sensor 140 (i.e., at +30 mm) at the start of movement, namely, at time zero (at the beginning of rotation of a pulse motor when the pulse motor is used to drive the grid 130). The grid 130 moves to a position of a value that is determined by equation of 30 cos (ωt) (ω is an angular speed of the pulse motor), and reaches to a point 30 mm left of the center line CL1 of the sensor 140 (i.e., at −30 mm) at time 200 ms. The grid 130 returns toward the center line CL1 of the sensor 140 from the point 30 mm left thereof, and then reaches to the point 30 mm right of the center line CL1 of the sensor 140 (namely, at the start point) at time 400 ms.

The grid 130 moves reciprocatingly in front of the sensor 140 as shown in FIG. 2. In this case, the grid 130 momentarily stops and resumes a turn movement at the end of the reciprocating movement (for example, at the point 30 mm left of the center line CL1 of the sensor 140 (i.e., at −30 mm)).

When the grid 130 turns in this way, the grid 130 momentarily stops moving. In case that the X rays irradiating the object 120 and transmitted through the object 120 enter the sensor 140 when the grid 130 momentarily comes to a halt, a striped pattern attributable to the grid 130 distinctly appears in the resulting X-ray image. In other words, the moire pattern due to the grid 130 becomes pronounced in the resulting X-ray image obtained by the X-ray image acquisition unit 150.

To make the striped pattern attributable to the grid 130 less visible in the resulting X-ray image, the grid 130 needs to be controlled such that exposure of the object 120 to the X rays ends before the grid 130 reaches a turning point thereof.

The position of the grid 130 with respect to the sensor 140 at the start of the X-ray exposure will now be discussed.

Now the object 120 is irradiated with X-ray with the grid 130 passing the zero point as shown in FIG. 2 (for a predetermined duration of time with the grid 130 being in the vicinity of the zero point) when the grid 130 moves fast. The intensity distribution of the X rays obtained by the X-ray image acquisition unit 150 is less subject to the cutoff effect of the grid 130. Since the movement speed of the grid 130 is the fastest in the vicinity of the zero point along the path of the grid 130, contrast of the striped pattern due to the grid 130 is minimized in the resulting X-ray image.

Exposure of the object 120 to the X rays now starts with the grid 130 moving slowly in the vicinity of the start point of the movement (at 30 mm) as shown in FIG. 2. In this case, the object 120 can be irradiated with X rays for a relatively long time from the start of the movement of the grid 130 to the turning point thereof.

The grid movement controller 170 includes the grid position measurement unit 175 to measure the position of the grid 130 in the movement thereof as discussed above.

FIG. 4 shows an example of the grid position measurement unit 175. Referring to FIG. 4, there are shown the grid 130, and a link mechanism 410 which converts the rotary motion of the pulse motor into a reciprocating movement of the grid 130. A notch 420 is formed in a rotary disk 430.

The rotary disk 430 having the notch 420 is attached to the rotary shaft of the pulse motor for driving the grid 130. An initial position of the pulse motor is determined by detecting light, emitted by an unshown LED (Light Emitting Diode), through the notch 420 using a photosensor such as a photodiode. When the grid 130 starts moving, the grid position measurement unit 175 counts the number of pulses that are fed to drive the pulse motor, thereby determining the angle of rotation of the pulse motor, and thereby determining the position of the grid 130.

The grid position measurement unit 175 shown in FIG. 4 is an exemplary construction. The grid position measurement unit 175 is not limited to the exemplary construction shown in FIG. 4. Alternatively, the position of the grid 130 itself may be measured, and the results of measurement may be fed to the grid movement controller 170.

There occurs a delay time from the pressing of the X-ray exposure button 210 to the actual exposure of the object 120 to X rays from the X-ray emitter 110 (an X-ray generator, for example). To match the movement of the grid 130 and the driving of the sensor 140 with the irradiation of X rays from the X-ray emitter 110 in timing, a delay time needs to be measured beforehand from the pressing of the X-ray exposure button 210 (more precisely, from the supply of an X-ray exposure start signal to the X-ray emitter 110) to the actual irradiation of X rays from the X-ray emitter 110.

The X-ray timing acquisition unit 160 in the sensor 140 is used to measure the delay time. The X-ray timing acquisition unit 160 has the function of chronologically or successively measuring the intensity of X rays emitted from the X-ray emitter 110 subsequent to the pressing of the X-ray exposure button 210.

Figure 5:
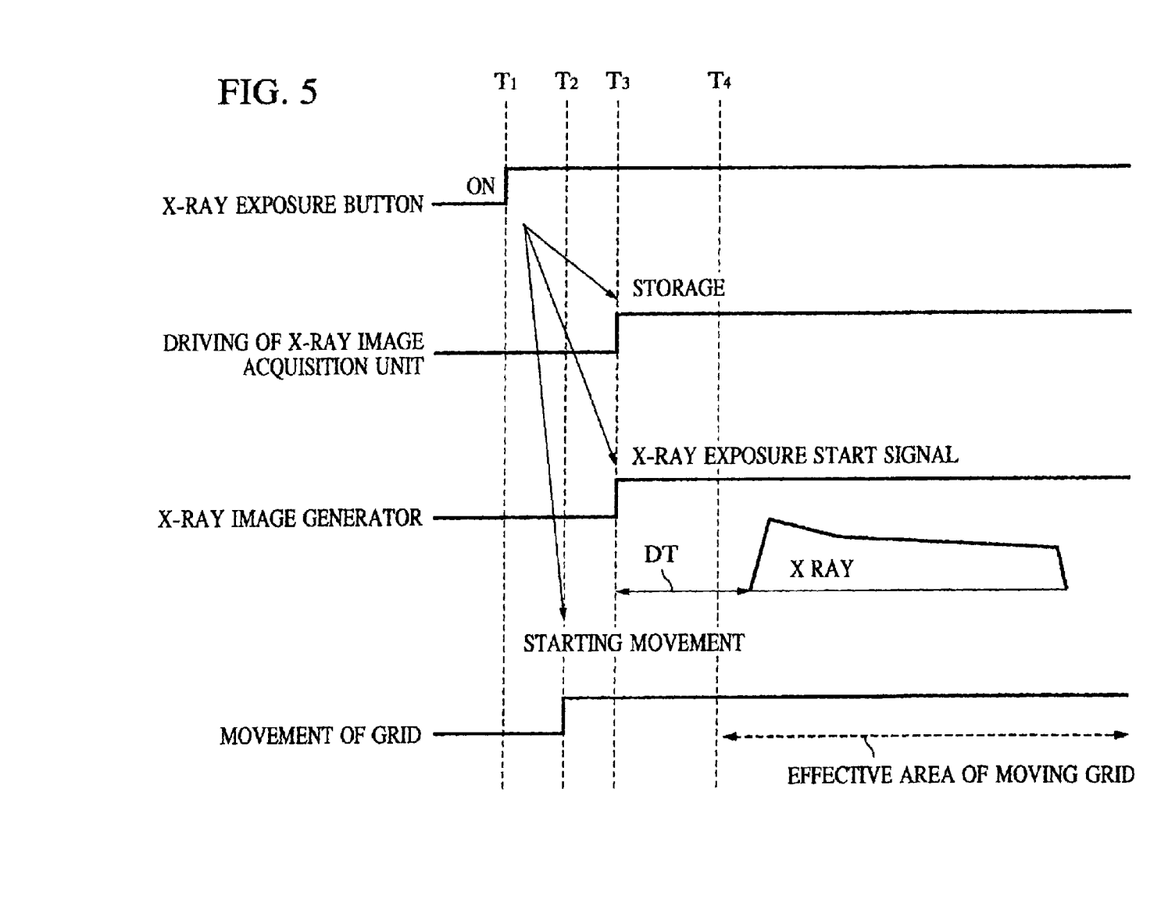
FIG. 5 is a timing diagram illustrating timings of the movement of the grid, operation of the sensor, and irradiating X rays.

Referring to FIG. 5, the timings of the movement of the grid 130, the driving of the sensor 140, and the irradiation of X rays from the X-ray emitter 110 are discussed in greater detail below.

FIG. 5 is a timing diagram showing the timings of the movement of the grid 130, the driving of the sensor 140, and the irradiation of X rays.

Referring to FIG. 5, the X-ray exposure button 210 is pressed to begin X-ray exposure at time $T_1$. The grid movement controller 170 controls the grid 130 at time $T_2$ after a predetermined time elapsed from time $T_1$ to move the grid 130. The predetermined time is determined so that the effective duration of time of the moving grid (corresponding to an effective area) shown in FIG. 2 and FIG. 4 includes a duration of time (assumed exposure time) during which the X rays are irradiated from the X-ray emitter 110.

At time $T_3$, the X-ray image acquisition unit 150 starts an accumulation operation for accumulating the X ray signal transmitted through the object 120. The accumulation operation lasts until the intensity of the X rays acquired by the X-ray timing acquisition unit 160 becomes zero. At time $T_3$, the X-ray exposure start signal is fed to the X-ray emitter 110, and the X-ray emitter 110 begins generating X rays. The X-ray emitter 110 has a delay time DT, characteristic of the X-ray generator, from the supply of the X-ray exposure start signal to the actual irradiation of X rays. The delay time DT is measured (beforehand) using the X-ray timing acquisition unit 160, and then the start time of the accumulation operation by the X-ray image acquisition unit 150 is determined (i.e., the start time of the accumulation operation is delayed by a predetermined time from the supply time of the X-ray exposure start signal with the delay time DT accounted for).

The X-ray timing acquisition unit 160 measures the delay time DT. If the X-ray image acquisition unit 150 has the function of successively measuring the intensity of X rays, the X-ray image acquisition unit 150 may measure the delay time without using the X-ray timing acquisition unit 160. Alternatively, the X-ray timing acquisition unit 160 may be arranged in the X-ray emitter 110 rather than in the sensor 140.

Figure 6:
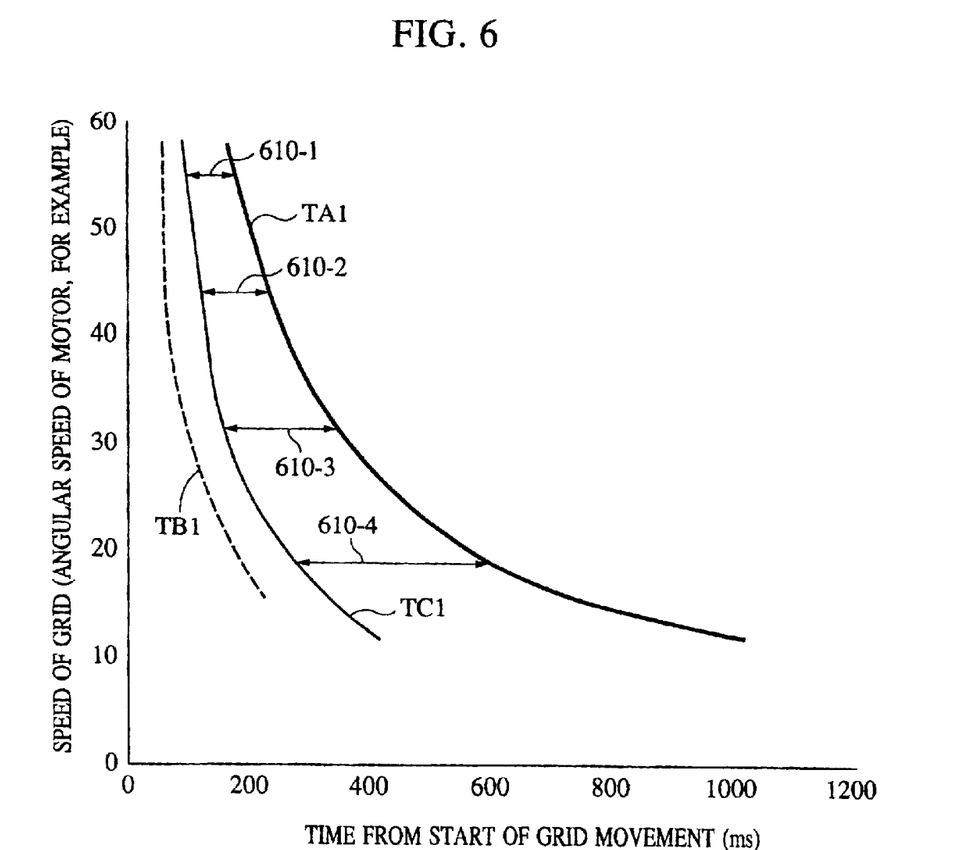
FIG. 6 is a graph for determining an exposure time of the X rays.

FIG. 6 is a graph for determining the X-ray exposure time duration in case that the grid 130 reciprocatingly moves in front of the sensor 140. The abscissa represents the elapsed time from the beginning of the movement of the grid 130, while the ordinate represents the angular speed of the pulse motor corresponding to the movement speed of the grid 130.

As shown, TA1 represents the time from when the grid 130 starts moving until when the grid 130 reaches the turning point. Specifically, TA1 indicates a reference intended to stop the exposure of the object 120 to the X rays before the turning point of the grid to reduce the contrast of the striped pattern due to the grid in the resulting X-ray image acquired by the X-ray image acquisition unit 150.

TB1 represents the time from when the grid 130 starts moving until when the X-ray emitter 110 starts directing X rays to the object 120, i.e., the time from when the grid 130 starts moving until the grid 130 reaches a position where the start of the irradiation of X rays is appropriate. TC1 represents the time from when the grid 130 starts moving until the moire pattern due to the grid is reduced to predetermined degree subsequent to the start of the irradiation of X rays. Specifically, the duration of time from TB1 to TC1 is the time needed for the required number of lead foil lines takes to pass by a single pixel of the X-ray image acquisition unit 150 from the beginning of the irradiation of X rays to reduce the moire pattern due to the grid to predetermined degree.

The number of passing lead foil lines of the grid 130 is obtained by dividing the product of the movement speed of the grid and the irradiation time of the X rays (i.e., the time integral of the grid movement speed, namely, the distance of travel of the grid) by the pitch of the lead foil of the grid 130. When the movement speed of the grid 130 and the pitch of the lead foils of the grid 130 are determined, a required X-ray exposure time to reduce the moire pattern to predetermined degree is calculated from the required number of passing lead foil lines of the grid 130. The X-ray image acquisition unit 150 thus acquires the X-ray image free from the moire pattern by causing the X-ray emitter 110 to start the exposure of the object 120 to the X rays from TB1, and to end the exposure of the object 120 to the X rays for somewhere between any of durations 610-1, 610-2, 610-3, and 610-4 (i.e., between TC1 and TA1) as shown in FIG. 6.

By selecting (appropriate exposure time) appropriate one of the durations of time corresponding to the movement speed of the grid 130 (i.e., the angular speed of the pulse motor), a grid table is formed and stored in the imaging controller 180. The grid table is displayed on the operation display unit 230 on the imaging operation unit 220 so that an operator (a user) of the digital radiographic apparatus may utilize the grid table.

Specifically, the grid table is formed and displayed in the form of $T_S \leq T \leq T_E$ in accordance with the movement speed of the grid 130 (or the angular speed of the step motor), wherein $T_S$ represents a minimum X-ray exposure time and $T_E$ represents a maximum X-ray exposure time. The minimum X-ray exposure time $T_S$ is determined by subtracting the value of TB1 from the value of TC1 for each movement speed of the grid 130. The maximum X-ray exposure time $T_E$ is determined by subtracting the value of TB1 from the value of TA1 for each movement speed of the grid 130.

As described above, the digital radiographic apparatus tends to suffer from a degradation in the image quality of the X-ray image attributable to the moire pattern caused by the grid. Therefore, in X-ray imaging, the movement of the grid 130 needs to be precisely controlled. A time interval of the grid table $T_S \leq T \leq T_E$ is shorter than that permitted in the conventional film/screen system. A plurality of grid tables is thus prepared to permit a wide range of choice in the grid tables during X-ray imaging.

For example, when the chest of a human body is X-ray imaged, the X-ray exposure time is set to be as short as 10 ms so that a heart and the peripheral portion thereof are not blurred in the X ray image regardless of the heart beat. However, there are times when the X-ray exposure time becomes as long as one second because the transmittance of the X rays through the abdomen and the like of the human is typically low. To radiograph the human body, the digital radiographic apparatus must work with the exposure time ranging from several ms to several hundred ms or several seconds. Thus, a plurality of grid tables (for example, four or more grid tables) are required.

However, the use of multiple grid tables provided is accompanied by an inconvenience. The operator of the digital radiographic apparatus has difficulty in properly selecting the grid table appropriate for each X ray imaging application. In accordance with this embodiment, an imaging button corresponding to each region of the body to be imaged is arranged in the imaging operation unit 220, and is associated with the respective grid table. When the operator presses one imaging button, the grid table corresponding thereto is automatically selected. Based on the selected grid table, the grid movement controller 170 controls the movement of the grid 130.

In the imaging method that is set by an imaging button corresponding to each region of the body, a predetermined grid table chosen based on a standard imaging time (an X-ray exposure time) is selected.

Recently, imaging information (imaging request or ordering information) is transmitted and received through an HIS/RIS (Hospital Information System/Radiology Information System) system, and information for each region of the object (information concerning a region to be imaged) included in the imaging information is associated with a predetermined grid table. When the imaging information is received, the imaging controller 180 automatically selects a grid table matching the imaging information, and designates the movement speed of the grid 130 based on the selected grid table. The grid movement controller 170 controls the movement of the grid 130 in accordance with the designated movement speed of the grid 130, thereby appropriately moving the grid 130.

When the movement speed of the grid 130 is continuously varied, the minimum X-ray exposure time $T_s$ and the maximum X-ray exposure time $T_E$ in the grid table formed in accordance with FIG. 6 are substantially also continuously varied. A grid table $T_S \leq T \leq T_E$ thus selected is more appropriate for the imaging region than one grid table which is selected from a plurality of grid tables $T_S \leq T \leq T_E$ that are formed in response to the discretely selected movement speeds of the grid 130.

When the number of grid tables is increased to allow a grid table appropriate for an imaging region to be designated, a standard exposure time t is associated with the imaging region so that the operator easily selects an optimum grid table.

When the imaging button corresponding to the imaging region is pressed by the operator, or when the imaging information transmitted through the HIS/RIS system is received, the imaging controller 180 selects the standard exposure time t in response to the imaging button or the information concerning the imaging region in the imaging information, and then selects the grid table $T_S \leq T \leq T_E$ based on the standard exposure time t. The grid movement controller 170 thus controls the movement of the grid 130 in accordance with a grid table appropriate for the imaging region.

Figure 7:
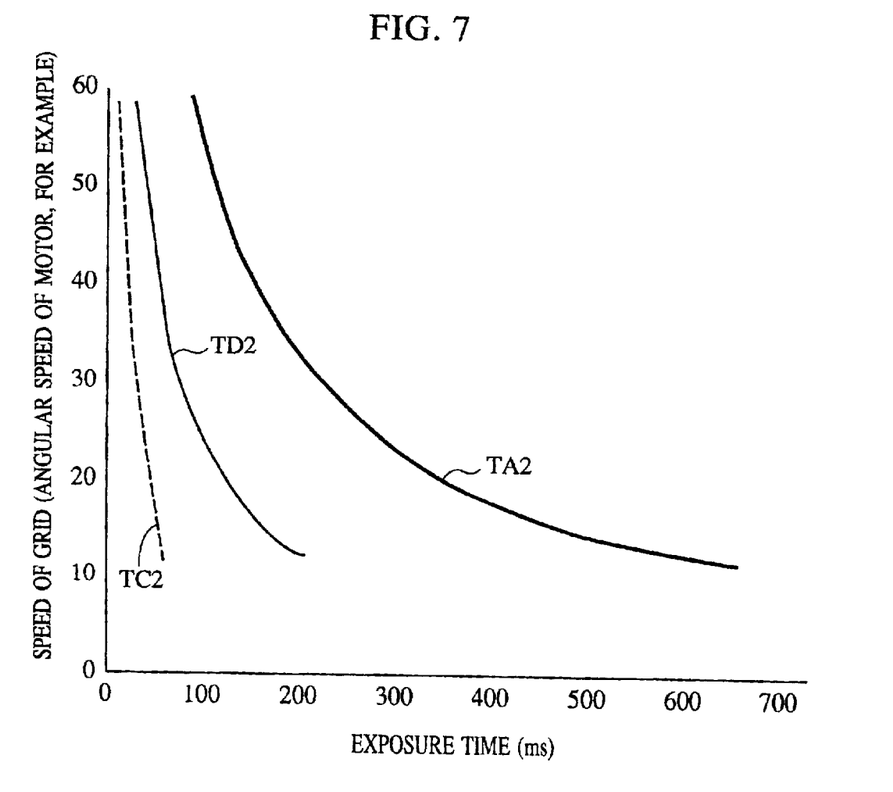
FIG. 7 is a graph plotting the interrelationship of standard X-ray exposure time, minimum X-ray exposure time, and maximum X-ray exposure time.

FIG. 7 is a graph plotting the interrelationship of the standard X-ray exposure time t, the minimum X-ray exposure time $T_S$, and the maximum X-ray exposure time $T_E$.

As shown, the abscissa represents the elapsed time (the X-ray exposure time) from when the X-ray emitter 110 has started irradiating the object 120 with the X rays, and the ordinate represents the movement speed of the grid 130. TA2 is a curve representing the maximum X-ray exposure time $T_E$, namely, the value that is obtained by subtracting the value of TB1 from the value of TA1 shown in FIG. 6. TC2 is a curve representing the minimum X-ray exposure time $T_S$, namely, the value that is obtained by subtracting the value TB1 from the value of TC1 shown in FIG. 6.

Each of the curves TA2 and TC2 is plotted against the X-ray exposure time along the abscissa on a one-to-one correspondence basis. Accordingly, the minimum X-ray exposure time $T_S$ and the maximum X-ray exposure time $T_E$ can be a function of the standard exposure time t, and are thus respectively expressed as the minimum X-ray exposure time $T_S(t)$ and the maximum X-ray exposure time $T_E(t)$.

The standard exposure time t is set to subdivide the time interval between the minimum X-ray exposure time $T_S(t)$ and the maximum X-ray exposure time $T_E(t)$ by a ratio of m:n (m and n are natural numbers) to tolerate a deviation of an actual exposure time from the standard exposure time t depending on a difference in the thickness of the object.

For example, TD2 shown in FIG. 7 indicates the standard exposure time t that is obtained by subdividing the time interval between the minimum X-ray exposure time $T_s(t)$ and the maximum X-ray exposure time $T_E(t)$ by a ratio of 5:2.

When the operator selects the imaging region, the standard exposure time t corresponding to the imaging region is selected using the interrelationship of the standard X-ray exposure time t, the minimum X-ray exposure time $T_S$, and the maximum X-ray exposure time $T_E$ shown in FIG. 7. Also selected are the grid table $T_S \leq T \leq T_E$ responsive to the standard exposure time t, and the movement speed of the grid 130. Thus, the grid movement controller 170 properly controls the movement of the grid 130.

Figure 8A:
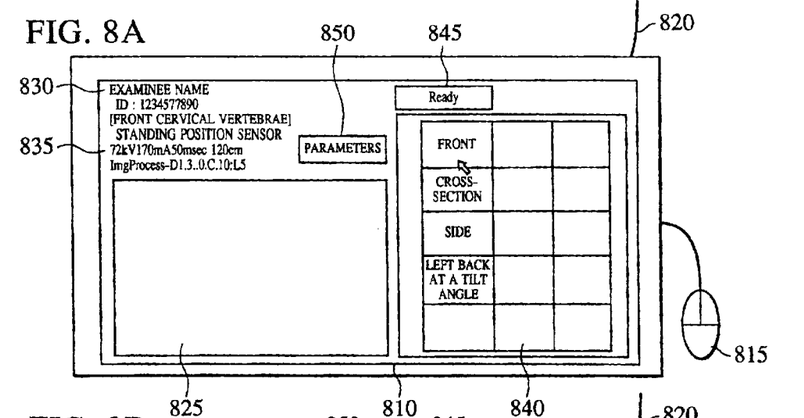
FIGS. 8A–8C illustrate operation screens of an operation display unit.
Figure 8B:
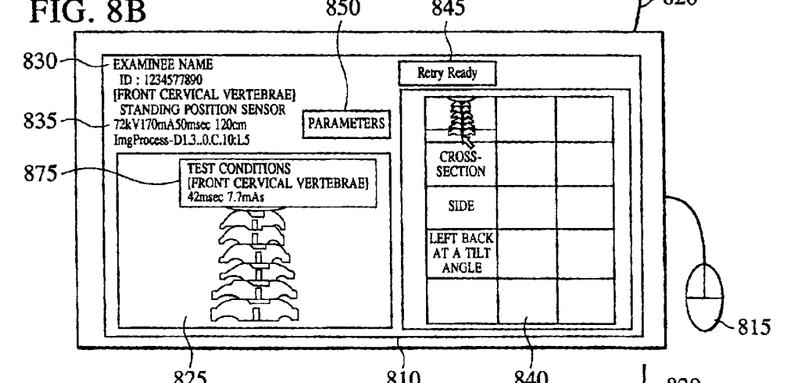
Figure 8C:
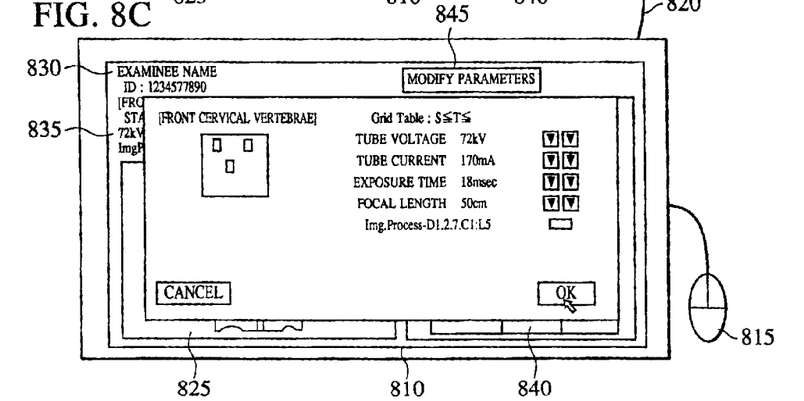

FIGS. 8A–8C illustrate example operation screens presented on the operation display unit 230 in the imaging operation unit 220.

Referring to FIG. 8A, a touch panel 810 includes a liquid-crystal display and an analog resistive-film touch sensor sheet. A mouse 815 is used to move a pointer on the display screen or to select an item on the display screen. Designated as 820 are cables for power and control lines.

The touch panel 810 presents a display of imaging operational parameters. The imaging operational parameters are selected and input by either the touch panel 810 or the mouse 815 or a combination thereof. The cables 820 include a power cable, a VGA (Video Graphics Array) cable, a touch panel controlling serial cable, and a mouse serial cable.

An image display area 825 displays a captured X-ray image. An object information display area 830 displays information relating to the object. An imaging method object parameter display area 835 displays parameters of an imaging method object. An imaging method object display area 840 displays an imaging method object in response to a status of the apparatus. A message display area 845 displays status and messages of the apparatus or a system. A modification button 850 is used in case that imaging conditions and/or image processing parameters are modified.

When X-ray imaging, the operator selects a desired imaging method object from among the imaging method objects displayed in the imaging method object display area 840. The selection of the imaging method object may be carried out by pressing the imaging method object displayed on the touch panel 810 or by sending the imaging information through the HIS/RIS system.

In the imaging method object, a number of imaging method parameters and standard imaging conditions corresponding to an imaging region are set. Since the standard exposure time t under the standard imaging conditions is associated with the grid table in one-to-one correspondence as already discussed with reference to FIG. 7, the grid table is also set in the imaging method object. Specifically, when the operator selects the imaging method object, the standard imaging time (the standard exposure time) t set beforehand corresponding to the selected imaging method object is displayed, and the grid table $T_s \leq T \leq T_E$ responsive to the standard imaging time t is thus selected.

When the X-ray exposure button 210 is pressed with a "Ready" message displayed on the message display area 845, the X-ray emitter 110 directs the X rays to the object 120, thereby X-ray imaging of the object 120 is performed. During X-ray imaging, the grid movement controller 170 moves the grid 130 as shown in FIGS. 2, 3, and 5.

When the object 120 is X-ray imaged in this way, the captured X-ray image is displayed on the image display area 825 as shown in FIG. 8B. When the modification button 850 is pressed with the image method object selected as shown in FIG. 8B, the display presented by the touch panel 810 changes to the one shown in FIG. 8C.

Referring to FIG. 8C, the touch panel 810 displays parameters required in X-ray imaging and sets those parameters corresponding to the selected imaging method object. The displayed parameters include exposure time, i.e., the standard exposure time. By modifying the exposure time using an up button or a down button, a grid table corresponding to a modified exposure time is displayed on the top portion of the screen.

In X-ray imaging, a function of adjusting a dose of X-ray irradiating the object, called an AEC (Auto Exposure Control) function, is available. However, X-ray imaging must be performed with an exposure time matching a grid table to obtain an X-ray image free from a moire pattern due to the grid. Further, as described above, a grid table corresponding to the imaging method object needs to be set. Therefore, if an actual exposure time adjusted through the AEC fails to match the grid table (the exposure time defined by the grid table), the grid table needs to be modified to match the actual exposure time.

The operation of automatic adjustment of the grid table performed when the actual exposure time fails to match the grid table is discussed below.

Figure 9:
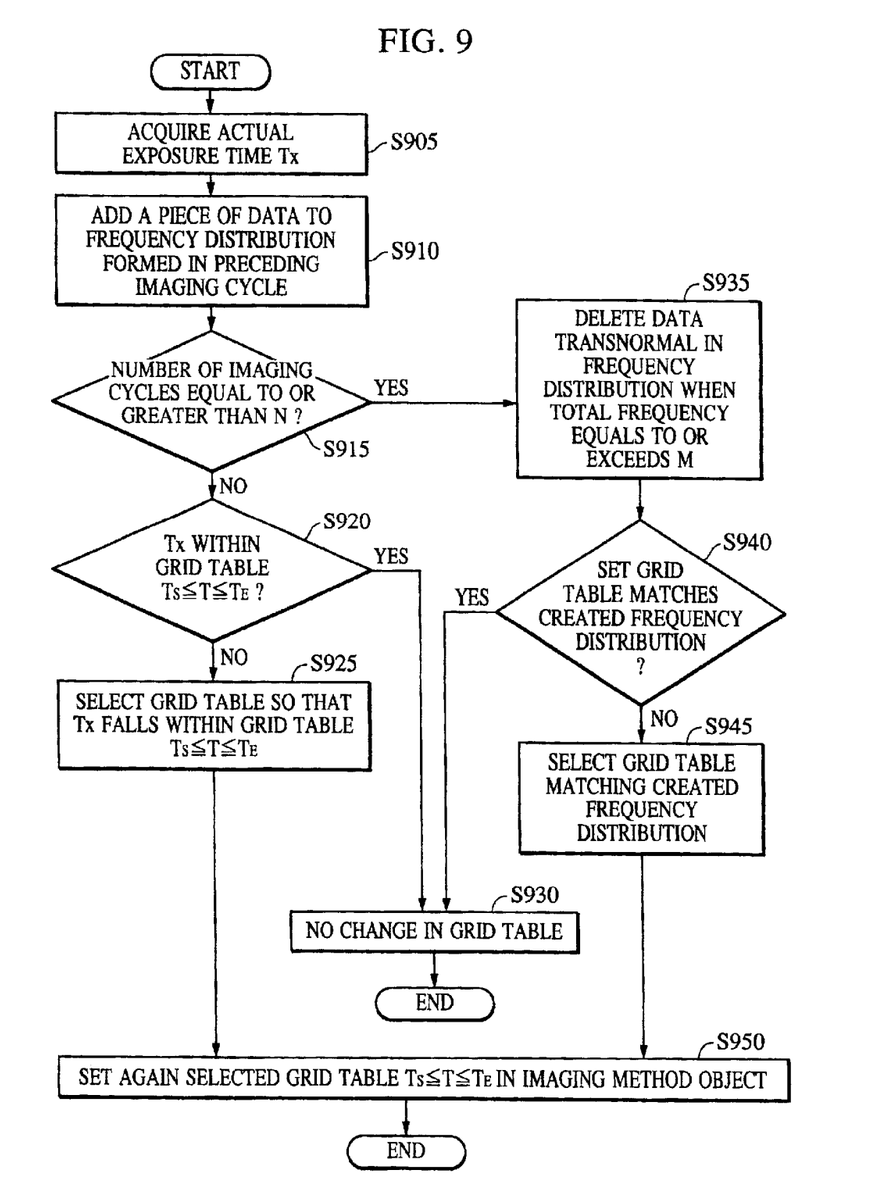
FIG. 9 is a flow diagram illustrating an operation in which a grid table is automatically adjusted when a set grid table fails to match an actual exposure time.

FIG. 9 is a flow diagram showing the operation of the automatic adjustment of the grid table performed when the actual exposure time fails to match the grid table. This operation is performed by the imaging controller 180.

When one imaging cycle is completed with the imaging method object selected, an actual exposure time $T_X$ of the object 120 to the X rays is acquired from the X-ray emitter 110 or the X-ray timing acquisition unit 160 in step S905, and is stored as data. In step S910, the X-ray exposure time $T_X$ acquired in step S905 is grouped according to intervals that are predetermined by discretely subdividing the X-ray exposure time, and a frequency distribution of the X-ray exposure time is formed (updated). Specifically, one piece of data (a frequency of one) is added to the frequency distribution of the X-ray exposure time formed at a preceding imaging cycle, in accordance with those discrete intervals.

In step S915, the imaging controller 180 determines whether the number of imaging cycles, including this imaging cycle, is equal to or greater than N with the same imaging method object selected.

When it is determined that the number of imaging cycles is less than N, the imaging controller 180 determines that a correct (appropriate) grid table can not be presumed from the frequency distribution based on the past X-ray exposure time. The frequency distribution is not used, but the acquired X-ray exposure time $T_X$ is used.

In step S920, the imaging controller 180 determines whether the currently acquired X-ray exposure time $T_X$ falls within the range of the grid table $T_S \leq T \leq T_E$. When it is determined that the currently acquired X-ray exposure time $T_X$ falls outside the range of the grid table $T_S \leq T \leq T_E$, the process proceeds to step S925. The imaging controller 180 newly selects a grid table $T_S \leq T \leq T_E$ within which the X-ray exposure time $T_X$ falls. This selection may be made so that the standard exposure time t discussed with reference to FIG. 7 equals the X-ray exposure time $T_X$, or so that a modification from the grid table $T_S \leq T \leq T_E$ for the current imaging is minimized.

When the new grid table is selected in step S925, the imaging controller 180 sets again the newly selected grid table to the imaging method object in step S950, and ends the process.

When it is determined in step S920 that the currently acquired X-ray exposure time $T_X$ falls within the range of the grid table $T_S \leq T \leq T_E$, the process ends without modifying the grid table (in step S930).

When it is determined in step S915 that the number of imaging cycles is equal to or greater than N, the imaging controller 180 proceeds the process to step S935 assuming that a correct grid table can be presumed from the frequency distribution based on the past X-ray exposure time.

Figure 10:
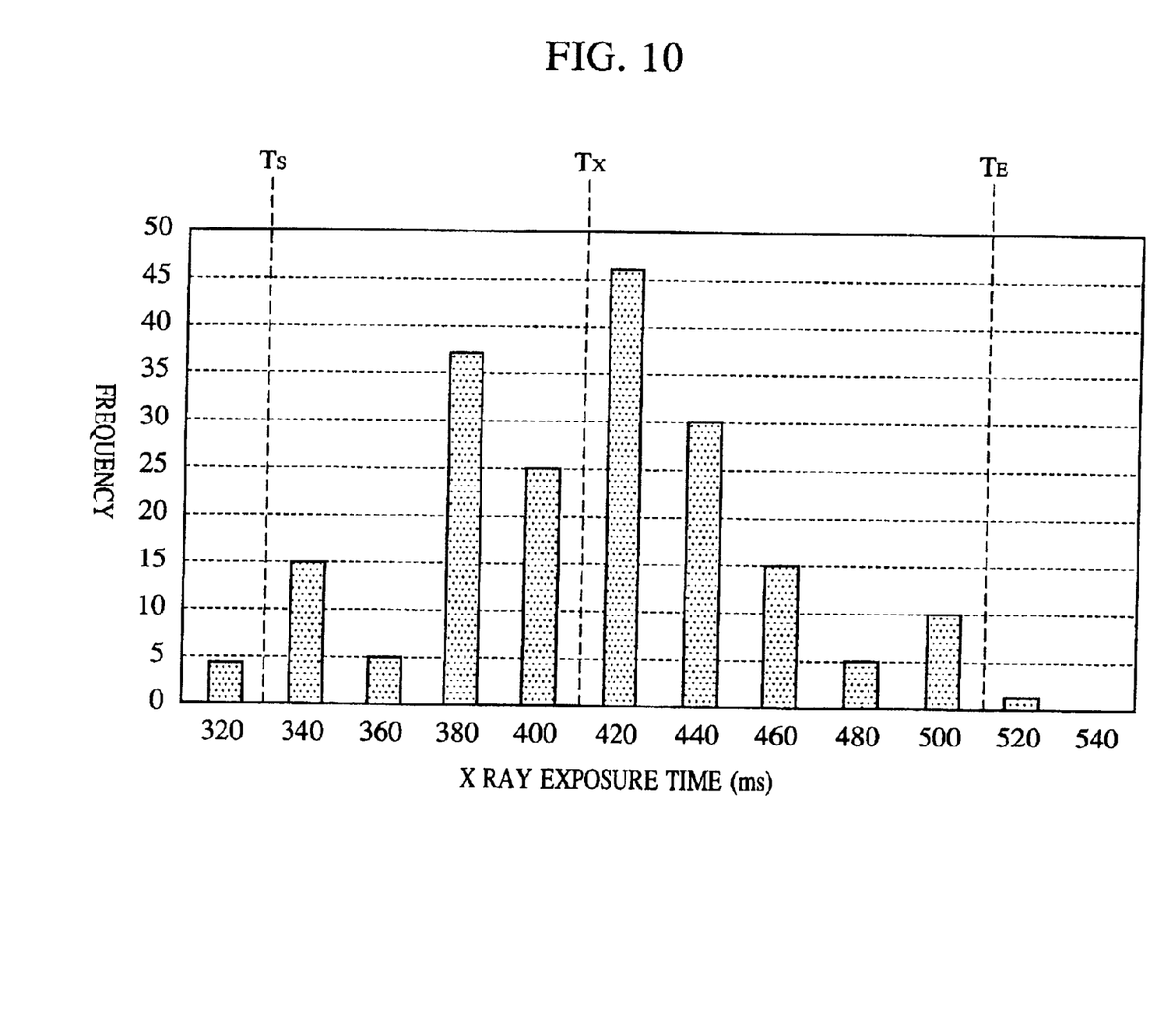
FIG. 10 plots an example of a frequency distribution.

The imaging controller 180 determines in step S935 whether the total frequency of the frequency distribution is equal to or more than M. When the total frequency is equal to or more than M, data transnormal in the frequency distribution is deleted (for example, data of X-ray exposure time having the lowest frequency is deleted). In step S940, the imaging controller 180 determines whether the currently set grid table $\leq T \leq T_S T \leq T_E$ is appropriate for the frequency distribution formed by the current imaging cycle. For example, in this determination, the imaging controller 180 references a difference between an expected value of the frequency distribution of the X-ray exposure time and the standard exposure time t shown in FIG. 7 currently set in the grid table, or performs a determination based on whether at least 80% elements of the frequency distribution satisfies the range of the grid table $T_S \leq T \leq T_E$. FIG. 10 shows an example of a frequency distribution.

When it is determined in step S940 that the frequency distribution of the X-ray exposure time fails to satisfy the range of the currently set grid table $T_S \leq T \leq T_E$, the process proceeds to step S945. The imaging controller 180 selects a grid table that meets the formed frequency distribution. In this selection, the imaging controller 180 selects a grid table, for example, so that an expected value of the frequency distribution of the X-ray exposure time substantially coincides with the standard exposure time t in the grid table shown in FIG. 7, or so that at least 80% elements of the frequency distribution satisfies the range of the grid table $T_S \leq T \leq T_E$.

When the new grid table is selected in step S945, the newly selected grid table is set again to the imaging method object in step S950, and the process ends.

When it is determined in step S940 that the frequency distribution of the X-ray exposure time satisfies the range of the currently set grid table $T_S \leq T \leq T_E$, the imaging controller 180 ends the process without modifying the grid table (in step S930).

As discussed above, while the X-ray emitter 110 directs the X rays to the object 120, the grid movement controller 170 controls the movement of the grid 130 so that the reciprocatingly moving grid 130 moves in one direction with a higher probability. The X-ray image acquisition unit 150 detects the X rays transmitted through the object 120 and the grid 130, and acquires an X-ray image in response to the intensity of the detected X rays.

Accordingly, the probability that when the grid 130 turns and moves the object 120 is still exposed to the X rays from the X-ray emitter 110 is reduced. In this way, the probability that the X-ray image acquisition unit 150 presents an X-ray image having less or no moire pattern due to the grid 130 is heightened.

The X-ray timing acquisition unit 160 measures the actual duration of time during which the object 120 is exposed to the X rays from the X-ray emitter 110. Based on the measured time, the configuration is provided that the grid movement controller 170 controls the movement of the grid 130 to increase the probability that the grid 130 moves in one direction during X-ray exposure (irradiation) time. In this way, the grid 130 is controlled at an appropriate speed and timing. Thus the probability that the X-ray image acquisition unit 150 provides an X-ray image with less or no moire pattern is heightened.

A standard time for exposing the object 120 to the X rays and/or an effective time duration including the standard exposure time are set as an X-ray exposure time. Parameters, such as the grid movement speed that is determined based on the X-ray exposure time, are set as the grid table for controlling the movement of the grid 130. The grid movement controller 170 thus controls the movement of the grid 130 in accordance with the grid table. By simply moving the grid 130 in accordance with the grid table, the probability that the reciprocatingly moving grid 130 moves in one direction during X-ray irradiation and that the X-ray image acquisition unit 150 acquires an X-ray image having less or no moire pattern due to the grid 130 is heightened.

Since the grid table used in X-ray imaging is displayed on the operation display unit 230, the operator judges from the actual X-ray exposure time whether an image with less or no moire pattern due to the grid 130 has been obtained. When the operator sets X-ray exposure time beforehand and radiographs the object 120, the operator has a chance, by the displayed grid table, to set an X-ray exposure time with which the probability that an image with less or no moire pattern due to the grid 130 is obtained is heightened.

Since a grid table is preset for each imaging method object displayed on the imaging operation unit 220, the operator easily selects the grid table that is preset appropriately for radiographing each region of an object, by simply selecting the imaging method object. This arrangement saves the labor time an operator may take to consider and then select the grid table at each imaging cycle.

The standard exposure time t is set to subdivide the time interval between the minimum X-ray exposure time $T_S$ and the maximum X-ray exposure time $T_E$ by a ratio of m:n (m and n are natural numbers), and the grid table is selected based on the standard exposure time t. When presetting the grid table for the imaging method object, the operator easily presets the grid table using the standard exposure time t as a guideline.

If the grid table set in each imaging method object is determined to fail to satisfy the actual X-ray exposure time (from statistics of past X-ray exposure times), the grid table satisfying the X-ray exposure time during imaging is automatically selected. The selected grid table is again set in the imaging method object. Even if a proper grid table is not set in one of score of imaging types, a grid table, which may be inappropriate, is replaced with another appropriate grid table which is considered more appropriate from the statistics of past X-ray exposure times.

The present invention has been discussed in connection with the digital radiographic apparatus using X-ray. However, the present invention is not limited to apparatuses using X rays. The present invention is applicable to apparatuses which obtain object images using other radiation transmitted by the object.

Modifications of the Embodiment of the Present Invention

A program code of software for carrying out the functions of the invention can be loaded into a computer in a system or an apparatus connected to a variety of devices so that the devices perform the functions of the invention. The variety of devices operate in accordance with the program stored in the computer (CPU or MPU) in the system or apparatus. The functions and process steps of the invention are thus carried out. Such embodiments fall within the scope of the present invention.

The program code of software performs the functions and the process steps of the invention. The program code itself, and means for feeding the program code to the computer, for example, a storage medium for storing the program code, fall within the scope of the present invention.

Available as storage media for storing the program code are a floppy disk, a hard disk, an optical disk, a magneto-optical disk, a CD-ROM, a magnetic tape, a nonvolatile memory card, ROM and the like.

By executing the program code read by the computer, the computer realizes the functions or performs the process steps of the invention. Furthermore, the functions or the process steps of the invention are realized or performed in cooperation with the OS (operating system) running on the computer or another application software program according to the instruction of the program code. Such a program code falls within the scope of the present invention.

The program code is read into a memory incorporated in a function expansion board in the computer or in a function expansion unit connected to the computer. The CPU mounted on the function expansion board or the function expansion unit performs partly or entirely the actual process in response to the instruction from the program code. The functions or the process steps of the invention are realized or executed through the process. Such a program code falls within the scope of the present invention.

The program code is delivered in a computer-readable storage medium. The program code may also be delivered on-line through a communication network such as the Internet.

While the present invention has been described with reference to what are presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An apparatus for radiographing an object, comprising:
an X-ray radiation unit for radiating X-ray;
a grid arranged in an X-ray radiation path;
a grid movement controller for changing a movement speed of the grid by changing a turn speed of a motor, comprising a link mechanism for changing a turn movement of the motor into a straight movement of the grid;
a sensor unit for converting the X-ray into image data;
an input unit for inputting information relating to a region of a body; and
an imaging controller for controlling (i) the time for the X-ray radiation unit to start radiating the X-ray, (ii) the time for the grid movement controller to start rotating the motor, and (iii) the time for the sensor unit to start storage, by associating one with another,
wherein the imaging controller (a) selects a standard radiation exposure time and the turn speed based on the information input into the input unit, (b) controls the radiation exposure starting time of the X-ray radiation unit based on the selection, and (c) causes the grid movement controller to rotate the motor at the turn speed,
wherein the standard radiation exposure time is selected based on the maximum X-ray radiation time to be determined according to the region of the body, and
wherein the imaging controller is configured such that it controls the radiation exposure starting time of the X-ray radiation unit so that the standard radiation exposure time will be y divided by a ratio of m:n, where y is the time interval between the minimum X-ray radiation time and the maximum X-ray radiation time, m and n are natural numbers, and the minimum X-ray radiation time and the maximum X-ray radiation time are determined according to the region of the body.

2. An apparatus according to claim 1, wherein the minimum X-ray radiation time is the time from when radiation starts until when the grid moves a predetermined distance, and the maximum X-ray radiation time is the time from when radiation starts until when the grid starts a turn movement.

3. An apparatus according to claim 2, wherein the predetermined distance is determined so that the value of the predetermined distance multiplied by a pitch of a lead foil of the grid will be a predetermined value.

4. An apparatus according to claim 1, further comprising a display unit for displaying one or more combinations of the minimum X-ray radiation time and the maximum X-ray radiation time, and the standard radiation exposure time.

5. An apparatus according to claim 1, wherein m is 5 and n is 2, and wherein the standard radiation exposure time is y/(5/2).

* * * * *

UNITED STATES PATENT AND TRADEMARK OFFICE
CERTIFICATE OF CORRECTION

PATENT NO. : 6,795,528 B2  
APPLICATION NO. : 10/035154  
DATED : September 21, 2004  
INVENTOR(S) : Makoto Nokita It is certified that error appears in the above-identified patent and that said Letters Patent is hereby corrected as shown below:

COLUMN 2  
Line 3, "is" should read --are--.

COLUMN 10  
Line 35, "parameters and" should read --parameters, especially--.  
Line 36, "region" should read --region,--.  
Line 39, "FIG. 7," should read --FIG. 7, information concerning--.  
Line 45, "thus selected" should read --also selected--.  
Line 52, "X-ray imaged" should read --radiographed--.  
Line 53, "image is" should read --image and the test conditions 875 corresponding to the image are--.  
Line 55, "image method" should read --imaging method--.

COLUMN 11  
Line 46, "$T_S \leqq T \leqq T_E$" should read --$T_S \leqq T \leqq T_E$--.

COLUMN 12  
Line 18, "$T_S \leqq T \leqq T_E$," should read --$T_S \leqq T \leqq T_E$,--.  
Line 45, "moves" should read --moves,--.

UNITED STATES PATENT AND TRADEMARK OFFICE
CERTIFICATE OF CORRECTION

PATENT NO. : 6,795,528 B2
APPLICATION NO. : 10/035154
DATED : September 21, 2004
INVENTOR(S) : Makoto Nokita It is certified that error appears in the above-identified patent and that said Letters Patent is hereby corrected as shown below:

COLUMN 13
Line 32, "set in" should read --preset for--.
Line 32, "object is" should read --object--.
Line 33, "determined to fail" should read --fails--.
Line 34 "(from statistics" should read --(this unsatisfaction is determined from statistics--.
Line 36 "selected" should read --newly-selected--.
Line 36, "set in" should read --set for--.
Line 37, "not set" should read --not preset--.
Line 38, "score" should read --scores--.
Line 39, "another appropriate" should read --another--.

Signed and Sealed this

Twenty-sixth Day of February, 2008

JON W. DUDAS
*Director of the United States Patent and Trademark Office*